US012758738B2

(12) United States Patent
Lee et al.

(10) Patent No.: US 12,758,738 B2
(45) Date of Patent: Oct. 13, 2026

(54) CUSTOMIZED-TYPE SLEEP MANAGEMENT METHOD AND SYSTEM

(71) Applicant: KOREA UNIVERSITY RESEARCH AND BUSINESS FOUNDATION, Seoul (KR)

(72) Inventors: Seong-Whan Lee, Seoul (KR); Hyeong-Jin Kim, Pohang-si (KR); Minji Lee, Seoul (KR); Gi-Hwan Shin, Daegu (KR)

(73) Assignee: Korea University Research and Business Foundation, Seoul (KR)

( * ) Notice: Subject to any disclaimer, the term of this patent is extended or adjusted under 35 U.S.C. 154(b) by 1202 days.

(21) Appl. No.: 17/612,290

(22) PCT Filed: Jun. 15, 2020

(86) PCT No.: PCT/KR2020/007684
§ 371 (c)(1),
(2) Date: Nov. 18, 2021

(87) PCT Pub. No.: WO2021/040206
PCT Pub. Date: Mar. 4, 2021

(65) Prior Publication Data

US 2022/0233805 A1 Jul. 28, 2022

(30) Foreign Application Priority Data

Aug. 29, 2019 (KR) ........................ 10-2019-0106311
Mar. 16, 2020 (KR) ........................ 10-2020-0031821

(51) Int. Cl.
*A61M 21/02* (2006.01)
*A61B 5/00* (2006.01)
(Continued)

(52) U.S. Cl.
CPC ........... *A61M 21/02* (2013.01); *A61B 5/4812* (2013.01); *A61B 5/4836* (2013.01);
(Continued)

(58) Field of Classification Search
CPC .......... A61M 21/02; A61M 2021/0022; A61M 2021/0027; A61M 2205/3569;
(Continued)

(56) References Cited

U.S. PATENT DOCUMENTS

2011/0301487 A1* 12/2011 Abeyratne ............. G16H 50/50 600/544
2016/0007914 A1* 1/2016 Xu ....................... A61B 5/7455 600/534
2019/0328996 A1* 10/2019 Lee ...................... A61B 5/7475

FOREIGN PATENT DOCUMENTS

KR 10-2008-0031952 A 4/2008
KR 10-0923968 B1 10/2009
(Continued)

OTHER PUBLICATIONS

Translation of KR 10-0923968B1 (Year: 2009).*
(Continued)

*Primary Examiner* — Carrie R Dorna
*Assistant Examiner* — Joshua Daryl D Lannu
(74) *Attorney, Agent, or Firm* — NSIP Law

(57) ABSTRACT

The present invention provides a customized sleep management method performed by a customized sleep management system including a step of collecting a bio-signal by using a computing device; a step of generating user sleep data by performing a pre-processing process on the collected bio-signal; a step of classifying sleep steps by using a sleep analysis model receiving the user sleep data and detecting sleep disorder appearing in the classified sleep steps; and a step of providing customized stimulation for alleviating the
(Continued)

detected sleep disorder. The bio-signal includes at least one of an electrophysiological signal and a non-electrophysiological signal.

15 Claims, 4 Drawing Sheets

(51) Int. Cl.

| | |
|---|---|
| ***A61B 5/0205*** | (2006.01) |
| ***A61B 5/24*** | (2021.01) |
| ***A61M 21/00*** | (2006.01) |
| ***G16H 20/70*** | (2018.01) |
| ***G16H 40/63*** | (2018.01) |
| ***G16H 40/67*** | (2018.01) |
| ***G16H 50/20*** | (2018.01) |

(52) U.S. Cl.
CPC ............ *A61B 5/7203* (2013.01); *A61B 5/725* (2013.01); *A61B 5/7267* (2013.01); *G16H 40/63* (2018.01); *A61B 2560/0223* (2013.01)

(58) Field of Classification Search
CPC ...... A61M 2205/3592; A61M 2230/10; A61M 2230/14; A61M 2230/50; A61M 2230/60; A61M 2230/63; A61B 5/4812; A61B 5/4836; A61B 5/7203; A61B 5/725; A61B 5/7267; A61B 2560/0223; A61B 5/02055; A61B 5/24; A61B 5/4815; G16H 40/63; G16H 40/67; G16H 50/20; G16H 20/70
See application file for complete search history.

(56) References Cited

FOREIGN PATENT DOCUMENTS

| | | | |
|---|---|---|---|
| KR | 10-2013-0087944 | A | 8/2013 |
| KR | 10-2014-0030489 | A | 3/2014 |
| KR | 10-2014-0039452 | A | 4/2014 |
| KR | 10-2014-0087902 | A | 7/2014 |
| KR | 10-2017-0083483 | A | 7/2017 |
| KR | 10-1763302 | B1 | 7/2017 |
| KR | 10-2018-0043114 | A | 4/2018 |
| KR | 10-2019-0049442 | A | 5/2019 |
| KR | 10-2004219 | B1 | 7/2019 |

OTHER PUBLICATIONS

Translation of KR 101516016B1 (Year: 2015).*
International Search Report issued on Sep. 24, 2020, in counterpart Korean Patent Application No. PCT/KR2020/007684 (2 pages in English).

* cited by examiner

CUSTOMIZED-TYPE SLEEP MANAGEMENT METHOD AND SYSTEM

CROSS-REFERENCE TO RELATED APPLICATIONS

This application is a U.S. National Stage Application of International Application No. PCT/KR2020/007684, filed on Jun. 15, 2020, which claims the benefit under 35 USC 119(a) and 365(b) of Korean Patent Application No. 10-2019-0106311 filed on Aug. 29, 2019, and Korean Patent Application No. 10-2020-0031821 filed on Mar. 16, 2020, in the Korean Intellectual Property Office, the entire disclosure of which is incorporated herein by reference for all purposes.

TECHNICAL FIELD

The present invention relates to a method and apparatus for detecting sleep disorder according to a sleep step and suggesting and adjusting optimal stimulation for alleviating the sleep disorder in order to increase sleep quality. More specifically, the present invention relates to a method and system for increasing sleep quality by classifying a sleep step and sleep disorder according to the sleep step by utilizing a user's bio-signal during sleep based on machine learning and suggesting customized optimal stimulation to effectively alleviate corresponding sleep disorder.

BACKGROUND

A human-computer interface is a technology that analyzes brain signals generated during various brain activities to recognize user intentions and control external devices therethrough. A user may control computers or machines through the human-computer interface without using muscles. The human-computer interface was mainly used to develop devices to assist motions of patients with kinetic disorder due to accident or disease.

Sleep is an important activity that maintains the body's circadian rhythm and enhances the body's recovery function. In particular, melatonin secreted from the brain during sleep not only acts as an antioxidant and anti-aging, but also regulates sleep rhythm to increase immunity through anti-cancer activity, blood pressure control, and stress relief. Such high-quality sleep is essential for maintaining a healthy life. However, according to the report of the organization for economic cooperation (OECD) in 2016, Korea ranked the lowest with 7 hours and 41 minutes in an "average sleep time by country survey". This is 41 minutes shorter than an average (8 hours 22 minutes), and office workers recorded 6 hours and 6 minutes, much lower than that. In addition, according to announcement of the National Health Insurance Corporation in 2013, the number of patients treated for sleep disorders is also rapidly increasing. Insufficient sleep or poor sleep quality may break the circadian rhythm and easily lead to weakened immunity, and these sleep disorders include, for example, insomnia, hypersomnia, sleep apnea, and somnambulism. Therefore, various methods for increasing sleep quality by alleviating sleep disorders are required.

Methods for treating the sleep disorders include drug therapy and stimulation therapy. Drugs for treating insomnia among sleep disorders include zolpidem, halcion, ativan, diazepam, and so on, and drugs for snoring or sleep apnea include atomoxenin and oxybutynin. However, these medications are only a temporary alternative to alleviate sleep disorders, and when taken for more than 2 to 3 weeks, tolerance develops to make it difficult to see effects, and when stopping taking the drugs, symptoms may get worse. Therefore, stimulation therapy is emerging as an alternative to alleviating sleep disorders. Treatment using sensory stimuli such as hearing, sight, and smell has advantages of being relatively easily used by ordinary people in real life and having relatively few side effects. However, existing technologies for detecting and alleviating sleep disorders detect specific sleep disorders to provide a notification service or suggest only appropriate stimulation. Since the technologies did not simultaneously detect various sleep disorders that degrade the sleep quality during sleep, application of the technologies had a limitation of not leading to increase in the sleep quality. In addition, since characteristics related to the sleep disorders cannot be accurately extracted by using only specific bio-signals such as electroencephalogram signals or electromyogram signals to detect sleep disorders, it is difficult to consider that sleep disorders are accurately detected.

Basically, sleep is mainly composed of non-rapid eye movement (NREM) sleep and rapid eye movement (REM) sleep. NREM sleep is a step in which rapid pupil movement does not occur and is further divided into three steps. First step (NREM1) is between sleep and wakefulness. During the first step of sleep, brain waves and muscle activity start to slow down, and representative brain waves at this time are theta waves (4 to 7 Hz). Second step (NREM2) is a step of light sleep, and in this step, a sleep spindle and K-complex are prominently displayed along with theta waves. The sleep spindle (12 to 14 Hz) and K-complex serve to suppress the body's response to external stimulation and protect sleep. Third step (NREM3) is a step of deep sleep and also known as slow wave sleep. During this step, the body responds less sensitively to the external environment, and the representative EEG is delta wave (0.5 to 4 Hz). Depending on the frequency of delta waves, it is sometimes divided into three steps and four steps. The REM sleep is a step in which rapid pupil movement occurs, during which a person usually dreams. Brain waves at this time appear similar to ae waking state. Sleep disorders do not appear continuously during sleep, but rather occur at a specific step of sleep. Therefore, there is a need for a method to accurately classify each sleep step in order to fundamentally increase a user's sleep quality, detect sleep disorders that may appear in the corresponding sleep step, and propose optimal stimulation to alleviate the sleep disorders.

The existing inventions have a limitation in that only one sleep disorder is detected, and determine a sleep state and occurrence of sleep disorders only with the user's non-electrophysiological signals during sleep without measuring the electrophysiological signal and do not use machine learning, and thus, there is a disadvantage that accuracy of accurate sleep step measurement and sleep disorder detection is reduced. In addition, since one person may have various sleep disorders, it is necessary to suggest a machine learning-based customized optimal stimulation that may accurately detect and effectively alleviate sleep disorders according to sleep steps.

SUMMARY OF INVENTION

Technical Problem

In order to solve the above-described problems, an object of an embodiment of the present invention is to detect accurate sleep step and various sleep disorders in real time by simultaneously analyzing an electrophysiological signal including brain waves and a non-electrophysiological signal including motion and sound and provide customized optimal stimulation according to the sleep disorders.

However, technical problems to be solved by the present embodiments are not limited to the technical problems described above, and there may be other technical problems.

Solution to Problem

According to a first aspect of the present disclosure, as a technical means for solving the above-described technical problems, a customized sleep management method performed by a customized sleep management system includes a step of collecting a bio-signal by using a computing device; a step of generating user sleep data by performing a pre-processing process on the collected bio-signal; a step of classifying sleep steps by using a sleep analysis model receiving the user sleep data and detecting sleep disorder appearing in the classified sleep steps; and a step of providing customized stimulation for alleviating the detected sleep disorder. The bio-signal includes at least one of an electrophysiological signal (EEG, EOG, EMG, or ECG) and a non-electrophysiological signal.

According to a second aspect of the present disclosure, as a technical means for solving the above-described technical problems, a customized sleep management system includes a measurement device including at least one measurement module for measuring a bio-signal; a stimulation providing device including at least one stimulation providing module for providing stimulation to a user; and a computing device that collects the bio-signal through the measurement device and provides customized stimulation through the stimulation providing device to alleviate sleep disorder in sleep steps classified by analysis of the collected bio-signal. The computing device includes a memory storing a customized sleep management program, and a processor for executing the program stored in the memory. The processor executes the customized sleep management program to collect the bio-signal measured by the measurement device, performs a pre-processing process on the collected bio-signal to receive user sleep data generated by performing pre-processing process for the collected bio-signal and to output sleep disorder information, and provides the customized stimulation matching the sleep disorder information through the stimulation providing device. The bio-signal includes at least one of an electrophysiological signal (EEG, EOG, EMG, or ECG) and a non-electrophysiological signal.

Advantageous Effects

According to a problem solving means of the present invention described above, it is possible to accurately determine a sleep step and sleep disorder by simultaneously analyzing an electrophysiological signal and a non-electrophysiological signal.

In addition, according to the problem solving means of the present invention, stimulation intensity may be adjusted by suggesting optimal stimulation capable of effectively alleviating each sleep disorder and continuously measuring a user's sleep state.

In addition, according to the problem solving means of the present invention, the user's sleep step and the sleep disorder are analyzed in real time to suggest customized optimal stimulation according thereto, and stimulation intensity according thereto is adjusted, and thus, sleep quality may be increased more effectively than existing technology.

MODE OF DISCLOSURE

Figure 1:
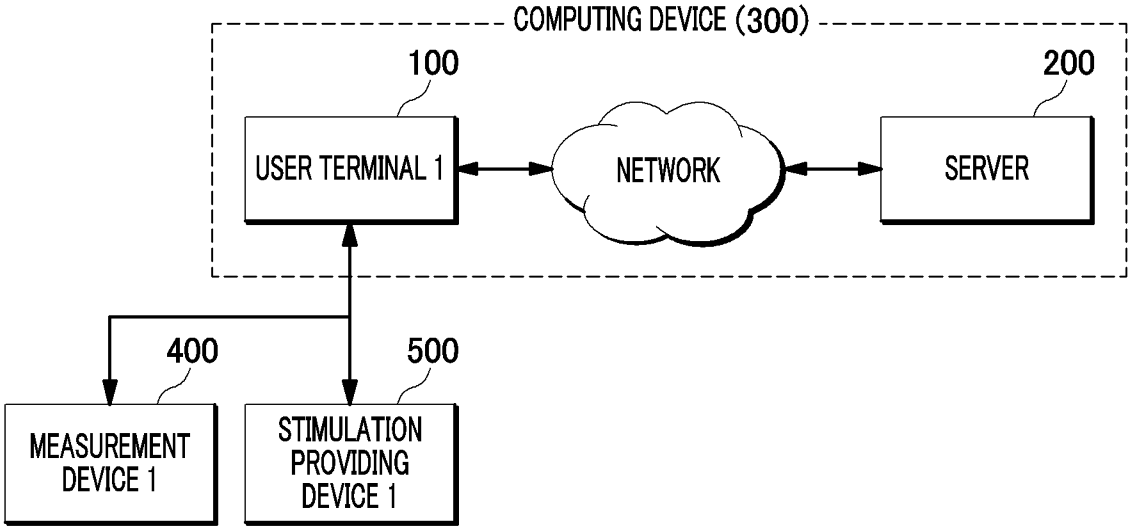
FIG. 1 is a block diagram illustrating a configuration of a customized sleep management system according to an embodiment of the present invention.

Hereinafter, embodiments of the present application will be described in detail with reference to the accompanying drawings such that those skilled in the art to which the present application belongs may easily implement the embodiments. However, the present application may be implemented in several different forms and is not limited to the embodiments described herein. In addition, in order to clearly describe the present application in the drawings, parts irrelevant to the description are omitted, and similar reference numerals are attached to similar components throughout the specification.

Throughout the present specification, when a portion is "connected" to another portion, this includes not only a case of being "directly connected", but also a case of being "electrically connected" with another component interposed therebetween. In addition, when a portion "includes" a component, this means that other components may be further included therein rather than excluding other components, unless otherwise stated, and it will be understood that the present invention does not preclude a possibility of presence or addition of one or more other features or numbers, steps, operations, components, portions, or combinations thereof.

In the present specification, a "terminal" may be a wireless communication device with guaranteed portability and mobility, and may be, for example, any type of handheld-based wireless communication device such as a smartphone, a tablet personal computer (PC), or a notebook computer. In addition, the "terminal" may also be a wired communication device such as a PC that may be connected to another terminal or a server through a network. In addition, the network indicates a connection structure capable of exchanging information between respective nodes such as terminals or servers, and includes a local area network (LAN), a wide area network (WAN), the Internet (World Wide Web (WWW)), a wired and wireless data network, a telephone network, and a wired and wireless television network.

For example, the wireless data communication network includes third generation (3G), 4G, 5G, third generation partnership project (3GPP), long term evolution (LTE), world interoperability for microwave access (WIMAX), Wi-Fi, Bluetooth communication, infrared communication, ultrasound communication, visible light communication (VLC), Li-Fi, and so on but are not limited thereto.

The following embodiments are detailed description to help understanding of the present invention, and do not limit the scope of the present invention. Accordingly, an invention of the same scope performing the same function as the present invention will also fall within the scope of the present invention.

FIG. 1 is a block diagram illustrating the configuration of a customized sleep management system according to an embodiment of the present invention.

A customized sleep management method may be performed by a computing device 300, a user terminal 100, or a server 200 linked to the user terminal 100. In the customized sleep management method, sleep data collection may be performed by one or more computing devices 300 and a measurement device 400. Analysis of the collected data may be performed by the server 200, and analysis result data may be provided to each user terminal 100. A plurality of users may each perform the customized sleep management method by using the computing device 300.

The user terminal 100 may be one of various devices, such as a smartphone, a tablet PC, a laptop computer, and a smart watch. The computing device 300 may include only the user terminal 100, and in this case, the measurement device 400 and a stimulation providing device 500 linked to the user terminal 100 may be used.

The measurement device 400 for measuring a bio-signal may measure an electrophysiological signal appearing when a user is sleeping and a non-electrophysiological signal. For example, the measurement device 400 may measure, for example, an electroencephalogram (EEG), an electromyography (EMG), an electrocardiogram (ECG), an electrooculogram (EOG) signal and a sound, a body temperature, and a motion signal of a user during sleep. The measurement device 400 may include a measurement module for each bio-signal to be measured.

The stimulation providing device 500 for providing a customized stimulation may provide a stimulation including at least one of sound, vibration, and light to a user in order to alleviate the detected sleep disorder.

According to an embodiment of the present invention, Optimal stimulation (sound, light, stimulation using an ultrasonic humidifier, vibration, temperature/humidity, electrical stimulation, and so on) may be suggested to a user according to the detected sleep disorder. For example, in a person who suffer from snoring, bruising, or in severe cases sleep apnea, a breathing passage (upper airway) such as a nasal passage or sinus are narrowed to cause oxygen to be not smoothly supplied to the brain, and thus, sleep quality is reduced. In this case, when fine water particles are sprayed into the nose by using an ultrasonic humidifier sensor module, an effect of widening the upper airway may be obtained, and thus oxygen may be smoothly supplied to the brain. As a result, a sleep disorder symptom of a user having sleep apnea may be alleviated to increase sleep quality. The stimulation providing device 500 may include a stimulation providing module for each stimulation type to be provided.

According to an embodiment of the present invention, after a stimulation is suggested, the user's sleep state is evaluated depending on whether or not the sleep disorder is alleviated in real time. When sleep disorder symptoms are not alleviated, stimulation intensity is adjusted again in consideration of user-specific characteristics.

In addition, according to an embodiment of the present invention, the measurement device 400 and the stimulation providing device 500 may be connected to the user terminal 100 by using a communication module 110 to configure a customized sleep management system. For example, the user terminal 100 is a personalization device such as a mobile phone or a tablet PC, and the measurement device 400 and the stimulation providing device 500 may be used in conjunction with the user terminal 100 by using short-distance communication such as Bluetooth, Wi-Fi, or Zigbee in the same type as a mobile accessory. In this case, a bio-signal measured by the measurement device 400 may be transmitted to the server 200 through the user terminal 100 to be analyzed by the server 200, and the analyzed result may be transmitted to the user terminal 100 again to be displayed, and a customized stimulation may also be transmitted from the server 200 to the stimulation providing device 500 via the user terminal 100 and then provided to a user.

Figure 2:
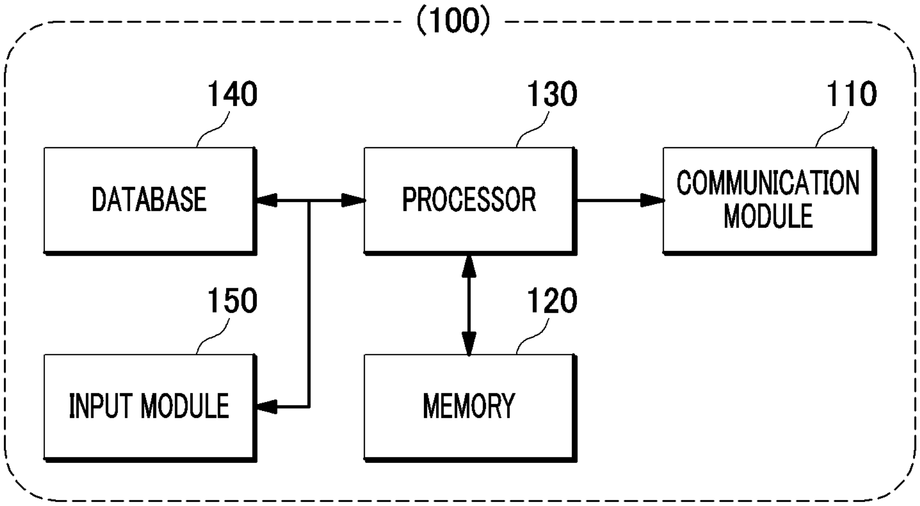
FIG. 2 is a block diagram illustrating a configuration of a user terminal in the customized sleep management system according to the embodiment of the present invention.

FIG. 2 is a block diagram illustrating a configuration of a user terminal in a customized sleep management system according to an embodiment of the present invention.

As illustrated in FIG. 2, a user terminal 100 of a customized sleep management system may include a communication module 110, a memory 120, a processor 130, a database 140, and an input module 150.

The communication module 110 communicates with the connected user terminal 100 and the linked server 200 to transmit or receive data. The communication module 110 may include hardware and software necessary for transmitting and receiving a signal such as a control signal or a data signal through wired/wireless connection to other network devices.

A customized sleep management program is stored in the memory 120. The customized sleep management program may collect bio-signals through a computing device, perform a pre-processing process on the collected bio-signals to generate user sleep data, classify sleep steps through a sleep analysis model by receiving the user sleep data, detect sleep disorder appearing in each of the classified sleep steps, and provide a customized stimulation for alleviating the detected sleep disorder.

The memory 120 stores an operating system for driving the customized sleep management server 200 or various data generated during execution of the customized sleep management program.

In this case, the memory 120 may include a non-volatile memory device that continuously maintains stored information even when power is not supplied, and a volatile memory device that requires power to maintain the stored information.

The processor 130 executes the program stored in the memory 120 and controls all processes according to execution of the customized sleep management program. Respective operations performed by the processor 130 will be described in more detail below.

The processor 130 may include any type of devices capable of processing data. For example, the processor 130 may indicate a data processing device embedded in hardware including a physically structured circuit to perform a function expressed as a code or a command included in a program. The data processing device embedded in hardware described above may include, for example, a microprocessor, a central processing unit (CPU), a processor core, a multiprocessor, an application-specific integrated circuit (ASIC), and a field programmable gate array (FPGA), and so on, but the scope of the present invention is not limited thereto.

The database 140 stores or provides data required for a customized sleep management system under the control of the processor 130. The database 140 may store, for example, an electrophysiological signal including an electroencephalogram signal, a non-electrophysiological signal including motion, sound, body temperature, and so on, and data of a specific frequency domain subjected to pre-processing, and also store data on sleep steps classified by the customized sleep management system, sleep disorder, sleep analysis data, and customized stimulation. The database 140 may be included as a component separate from the memory 120 or may be built in a partial region of the memory 120.

The server 200 may include a communication module, a memory, a processor, a database, and an input module, and a configuration and content thereof may be the same as the configuration and content of the user terminal 100. The customized sleep management method may be performed by the server 200 or may also be performed by the computing device 300 or the user terminal 100.

Figure 3:
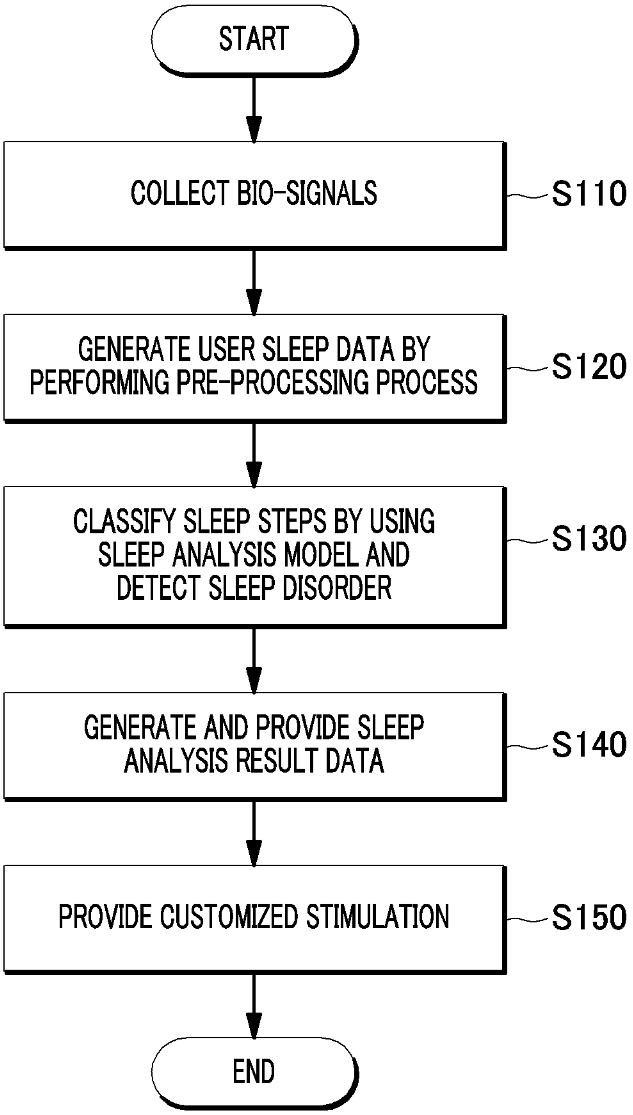
FIG. 3 is a flowchart illustrating a process sequence of a customized sleep management method according to an embodiment of the present invention.

FIG. 3 is a flowchart illustrating a process sequence of a customized sleep management method according to an embodiment of the present invention.

The processor 130 may collect bio-signals through the computing device (S110). The bio-signal may include at least one of an electrophysiological signal (EEG, EOG, EMG, or ECG) and a non-electrophysiological signal (sound, body temperature, or motion).

The computing device is a human-computer interface device and may include the user terminal 100, the measurement device 400, and the stimulation providing device 500. The user terminal may receive a bio-signal measured by the measurement device 400, and the customized stimulation may be provided by the stimulation providing device 500.

The bio-signal may include bio-signals measured from a waking state before sleep and may include bio-signals measured in real time according to a sleep step and sleep disorder after sleep starts.

The processor 130 generates user sleep data by performing a pre-processing process on the collected bio-signals (S120). The processor 130 may perform a pre-processing process such as removing noise unnecessary for analyzing a corresponding signal from the measured bio-signals and filtering the signal in a specific frequency band. For example, the processor 130 may perform a pre-processing process such as removing unnecessary noise to analyze the corresponding signal from the measured EEG data and filtering the signal in a specific frequency range (delta wave, theta wave, alpha wave, beta wave, gamma wave).

The processor 130 receives user sleep data and classifies sleep steps by using a sleep analysis model and detects sleep disorders appearing in the classified sleep steps.

The sleep analysis model may use a machine learning algorithm such as a support vector machine, an autoencoder, a convolution neural network, or recurrent neural network to analyze and classify in real time a user's sleep step based on information such as start time of each sleep steps, a frequency of a corresponding sleep step, and so on and may analyze and detect in real time sleep disorder that may appear in the corresponding sleep step by using the machine learning algorithm based on the classified sleep step and a user's bio-signal.

The measured EEG signal may be further analyzed to detect sleep disorder that may occur according to the classified sleep steps of Wake, NREM1, NREM2, NREM3, and REM. In addition, a user's sleep disorder may be detected in real time by simultaneously using pre-processed EMG, ECG, EOG signals, feature-extracted sound, body temperature, and motion signals. A representative sleep disorder for each sleep step includes insomnia in alpha/beta (Wake) state, bruising in theta (NREM1) step, sleep apnea in K-complex (NREM2), somnambulism in delta (NREM3), night terrors, restless legs syndrome in theta/beta (REM), behavioral disorder, and so on.

The processor 130 may generate sleep analysis result data and provide the sleep analysis result data to the computing device (S140).

The processor 130 may generate sleep analysis result data including at least one of a sleep step, a sleep disorder, a sleep step time, whether or not to detect a sleep disorder, life quality data, a customized stimulation type, and a customized stimulation intensity, and may provide the sleep analysis result data to the computing device via a visualized user interface.

The processor 130 may receive user information including one or more of age, gender, height, and weight in addition to the user sleep data and calibrates the user sleep data to correct a difference between bio-signals for each user based on the user information. In this case, characteristics of a brain signal changes depending on characteristics of a user's age, gender, and so on for each sleep step, and thus, a frequency band, an amplitude, a power spectrum, sleep spindle density, a sleep spindle duration, and so on which are representative for each sleep step and are characteristics of a brain signal, may be considered for calibration.

The processor 130 may provide a customized stimulation to alleviate the detected sleep disorder (S150).

The processor 130 may provide a user with a stimulation including one or more of sound, vibration, and light to alleviate the detected sleep disorder. Optimal stimulation (sound, light, stimulation using an ultrasonic humidifier, vibration, temperature/humidity, electrical stimulation, and so on) may be suggested to a user according to the detected sleep disorder. For example, in a person who suffer from snoring, bruising, or in severe cases sleep apnea, a breathing passage (upper airway) such as a nasal passage or sinus are narrowed to cause oxygen to be not smoothly supplied to the brain, and thus, sleep quality is reduced. In this case, when fine water particles are sprayed into the nose by using an ultrasonic humidifier sensor module, an effect of widening the upper airway may be obtained, and thus oxygen may be smoothly supplied to the brain. As a result, a sleep disorder symptom of a user having sleep apnea may be alleviated to increase sleep quality.

In addition, an auditory stimulation is effective for insomnia, visual stimulation and auditory stimulation are effective for sleep hallucination, electrical stimulation and vibration stimulation are effective for sleep paralysis, stimulation using temperature/humidity and electrical stimulation are effective for jet lag, shift work disorder, and restless legs syndrome, electrical stimulation and visual stimulation and auditory stimulation are effective for somnambulism and night terror, electrical stimulation is effective for enuresis, and electrical stimulation and visual stimulation and auditory stimulation are effective for REM sleep behavior disorder.

After the stimulation is suggested, the processor 130 evaluates a user's sleep state whether or not the sleep disorder is alleviated in real time. When the sleep disorder symptoms is not alleviated, the stimulation intensity may be adjusted again in consideration of characteristics of each user. the stimulation intensity according to a user's condition may be adjusted by considering the fact that optimal stimulation intensity required to alleviate the sleep disorder changes according to characteristics such as age, gender, and so on of a user.

Figure 4:
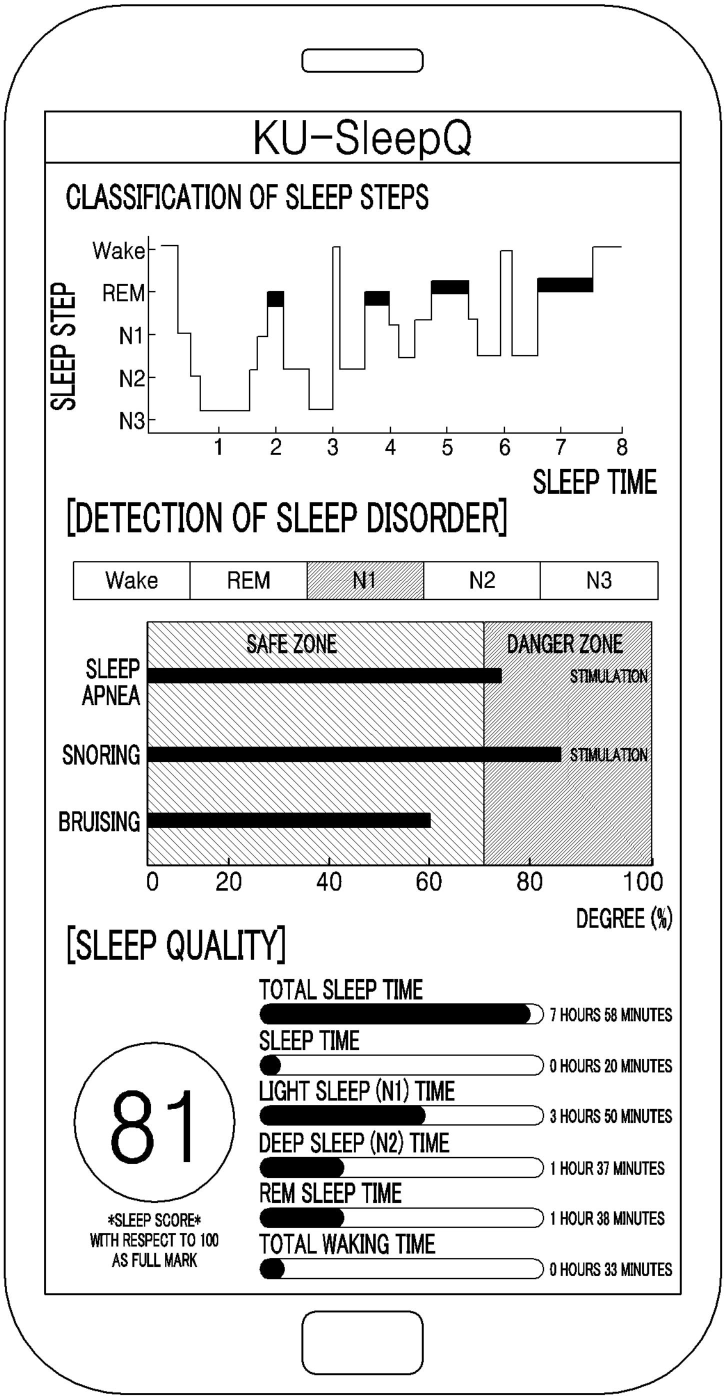
FIG. 4 is a diagram illustrating sleep analysis result data of a visualized user interface provided by the customized sleep management method according to the embodiment of the present invention.

FIG. 4 is a diagram illustrating sleep analysis result data on a visualized user interface provided by the customized sleep management method according to the embodiment of the present invention.

On the visualized user interface, sleep steps for each sleep time may be illustrated in a graph. The sleep steps may be classified into Wake, NREM1, NREM2, NREM3, and REM.

In addition to the EEG signal measured at each sleep step, the detected sleep disorder may be illustrated in a graph along with a degree thereof by simultaneously using the pre-processed EMG, ECG, and EOG signals and the feature-extracted sound, body temperature, and motion signals. Representative sleep disorder for each sleep step includes insomnia in alpha/beta (Wake) state, bruising in theta (NREM1) step, sleep apnea in K-complex (NREM2), somnambulism in delta (NREM3), night terrors, restless legs syndrome in theta/beta (REM), behavioral disorder, and so on.

When a degree of sleep disorder exceeds a preset reference, a necessary stimulation may be suggested. Optimal stimulation (sound, light, stimulation using an ultrasonic humidifier, vibration, temperature/humidity, electrical stimulation, or so on) may be suggested to a user according to the detected sleep disorder. For example, in a person who suffer from snoring, bruising, or in severe cases sleep apnea, a breathing passage (upper airway) such as a nasal passage or sinus are narrowed to cause oxygen to be not smoothly supplied to the brain, and thus, sleep quality is reduced. In this case, when fine water particles are sprayed into the nose by using an ultrasonic humidifier sensor module, an effect of widening the upper airway may be obtained, and thus oxygen may be smoothly supplied to the brain. As a result, a sleep disorder symptom of a user having sleep apnea may be alleviated to increase sleep quality.

In addition, an auditory stimulation is effective for insomnia, visual stimulation and auditory stimulation are effective for sleep hallucination, electrical stimulation and vibration stimulation are effective for sleep paralysis, stimulation using temperature/humidity and electrical stimulation are effective for jet lag, shift work disorder, and restless legs syndrome, electrical stimulation and visual stimulation and auditory stimulation are effective for somnambulism and night terror, electrical stimulation is effective for enuresis, and electrical stimulation and visual stimulation and auditory stimulation are effective for REM sleep behavior disorder.

Sleep quality may be evaluated by several criteria. Sleep evaluation indicators include time taken to enter NREM1 (Time to sleep), the number of wakes after falling asleep (Wake after sleep onset), total sleep time, a duration of a deep sleep (NREM3) step, sleep efficiency, and so on. In addition, a method of alleviating a sleep disorder symptom is also one of important criteria for sleep quality. Therefore, a user's sleep quality is evaluated based on the indicators.

The present invention may detect an accurate sleep step and various sleep disorders in real time by simultaneously analyzing electrophysiological signals including brain waves and non-electrophysiological signals including motion and sound and may provide customized optimal stimulation according to sleep disorder, and thus, sleep quality may be effectively increased.

Meanwhile, a method according to an embodiment of the present invention may also be implemented in the form of a recording medium including commands executable by a computer, such as a program module executed by the computer. Computer readable media may be any available media that may be accessed by a computer and includes both volatile and nonvolatile media, and removable and non-removable media. In addition, the computer readable media may include computer storage media. The computer storage media includes both volatile and nonvolatile media, and removable and non-removable media implemented by any method or technology for storing information such as computer readable commands, data structures, program modules, or other data. Although the method and system of the present invention are described with reference to specific embodiments, some or all of components or operations thereof may be implemented by using a computer system having a general purpose hardware architecture.

The above description of the present application is for illustration, and those skilled in the art to which the present application belongs will understand that the present invention may be easily modified into other specific forms without changing the technical idea or essential characteristics of the present application. Therefore, it should be understood that the embodiments described above are illustrative in all respects and not restrictive. For example, each component described as a single type may be implemented in a distributed manner, and likewise components described as distributed may also be implemented in a combined form.

The scope of the present application is indicated by the following claims rather than the above detailed description, and all changes or modifications derived from the meaning and scope of the claims and their equivalent concepts should be construed as being included in the scope of the present application.

SIGNS LIST

10: system
100: user terminal
110: communication module
120: memory
130: processor
140: display module
150: input module
200: server
300: computing device
400: measurement device
500: stimulation providing device

The invention claimed is:

1. A customized sleep management method performed by a customized sleep management system, the method comprising:

collecting a bio-signal by using a computing device;

generating user sleep data by performing a pre-processing process on the collected bio-signal;

classifying sleep steps by using a sleep analysis model receiving the user sleep data and detecting a sleep disorder appearing in the classified sleep steps; and providing customized stimulation for alleviating the detected sleep disorder, wherein the bio-signal includes a pre-sleep bio-signal measured in an awake state before sleep and a post-sleep bio-signal measured in real time according to a sleep step and the detected sleep disorder after sleep starts, and wherein providing the customized stimulation further comprises:

monitoring, in real time, a sleep state of the user after providing the customized stimulation;

determining a degree of alleviation of the sleep disorder based on the monitored sleep state; and dynamically adjusting an intensity of the customized stimulation based on one or more user-specific characteristics when symptoms of the sleep disorder are not alleviated beyond a threshold level.

2. The customized sleep management method according to claim 1, wherein the computing device includes a user terminal, a measurement device, and a stimulation providing device as a human-computer interface device, wherein the user terminal receives the bio-signal measured by the measurement device, and wherein the customized stimulation is provided through the stimulation providing device.

3. The customized sleep management method according to claim 1, further comprising:

removing noise included in the collected bio-signal during the pre-processing process; and extracting a preset frequency signal region for sleep step classification through frequency filter.

4. The customized sleep management method according to claim 1, wherein the sleep analysis model is configured to:

classify the sleep steps through machine learning based on the user sleep data including sleep start time and frequency information, detect the sleep disorder appearing in the classified sleep steps, and use any one of machine learning algorithms including a support vector machine, an autoencoder, a convolution neural network, and a recurrent neural network.

5. The customized sleep management method according to claim 1, wherein the collecting the bio-signal further includes receiving user information including one or more of age, gender, height, and weight, wherein the generating the user sleep data further includes calibrating the user sleep data based on the user information, and wherein the classifying the sleep steps includes classifying the sleep steps by using the sleep analysis model receiving the user sleep data and the user information and detecting sleep disorder appearing in the classified sleep steps.

6. The customized sleep management method according to claim 1, wherein the providing the customized stimulation further includes:

generating sleep analysis result data including at least one of the sleep step, the sleep disorder, time for each sleep step, whether or not to detect sleep disorder, life quality data, a type of the customized stimulation, and the intensity of the customized stimulation, and providing the sleep analysis result data to the computing device through a visualized user interface.

7. The customized sleep management method according to claim 1, wherein the providing the customized stimulation further includes:

updating the sleep analysis result data changed by the customized stimulation.

8. A non-transitory computer-readable recording medium comprising a computer program for performing the method according to claim 1.

9. A customized sleep management system comprising:

a measurement device including at least one measurement module comprising at least one sensor configured to measure a bio-signal;

a stimulation providing device including at least one stimulation providing module comprising an ultrasonic humidifier, temperature or electrical stimulator configured to provide stimulation to a user; and a computing device configured to collect the bio-signal through the measurement device and provide customized stimulation through the stimulation providing device to alleviate a sleep disorder in sleep steps classified by analysis of the collected bio-signal, wherein the bio-signal includes a pre-sleep bio-signal measured in an awake state before sleep and a post-sleep bio-signal measured in real time according to a sleep step and the sleep disorder after sleep starts, wherein the computing device includes a memory storing a customized sleep management program, and a processor for executing the program stored in the memory, wherein the processor executes the customized sleep management program to collect the bio-signal measured by the measurement device, performs a pre-processing process on the collected bio-signal to receive user sleep data generated by performing pre-processing process for the collected bio-signal and to output sleep disorder information, and provides the customized stimulation matching the sleep disorder information through the stimulation providing device, and wherein the processor is further configured to:

monitor, in real time, a sleep state of the user after the customized stimulation is provided;

determine a degree of alleviation of the sleep disorder based on the monitored sleep state; and dynamically adjust an intensity of the customized stimulation based on one or more user-specific characteristics when symptoms of the sleep disorder are not alleviated beyond a threshold level.

10. The customized sleep management system according to claim 9, wherein the computing device is a user terminal, and transmits the collected bio-signal to an external server configured to generate the user sleep data, input the user sleep data to a sleep analysis model operating in the external server and transmit analyzed results to the user terminal, and wherein the user terminal receives information on the customized stimulation generated by the external server and provides the information through the stimulation providing device.

11. The customized sleep management system according to claim 10, wherein the sleep analysis model classifies the sleep steps through machine learning based on the user sleep data including sleep start time and frequency information and detects the sleep disorder appearing in the classified sleep steps and uses any one of machine learning algorithms including a support vector machine, an autoencoder, a convolution neural network, and a recurrent neural network.

12. The customized sleep management system according to claim 10, wherein the processor is configured to further perform a step of receiving user information including one or more of age, gender, height, and weight through the computing device, calibrating the user sleep data based on the user information, and classifying the sleep steps by using the sleep analysis model receiving the user sleep data and the user information and detecting the sleep disorder appearing in the classified sleep steps.

13. The customized sleep management system according to claim 9, wherein, during the pre-processing process, noise included in the collected bio-signal is removed, and a preset frequency signal region for sleep step classification through frequency filtering is extracted.

14. The customized sleep management system according to claim 9, wherein the processor is configured to further perform generation of sleep analysis result data including at least one of the sleep step, the sleep disorder, time for each sleep step, whether or not to detect the sleep disorder, life quality data, a type of the customized stimulation, and the intensity of the customized stimulation, and provision of the sleep analysis result data to the computing device through a visualized user interface, after the customized stimulation is provided.

15. The customized sleep management system according to claim 9, wherein the processor is configured to further perform an update of sleep analysis result data changed by the customized stimulation and adjusting the intensity of the customized stimulation, after the customized stimulation is provided.

* * * * *